United States Patent [19]

Hofland

[11] Plant 5,128

[45] Oct. 25, 1983

[54] *NEPHROLEPIS EXALTATA*— ELEANOR CULTIVAR

[75] Inventor: G. Jack Hofland, Jordan Station, Canada

[73] Assignee: Jordan Station Wholesale Florist Limited, Jordan Station, Canada

[21] Appl. No.: 389,057

[22] Filed: Jun. 16, 1982

[51] Int. Cl.[3] ..... A01H 9/00

[52] U.S. Cl. ..... Plt./88

[58] Field of Search ..... Plt./88

*Primary Examiner*—Robert E. Bagwill

*Attorney, Agent, or Firm*—Burns, Doane, Swecker & Mathis

[57] ABSTRACT

The invention relates to a new and distinct variety of *Nephrolepis exaltata* which is believed to be a whole plant mutation of Curly Boston. The new variety is exceptionally good for growing as a houseplant or in a hanging basket. When compared with Curly Boston the new variety commonly exhibits a faster growth, fronds of a more oblong configuration, larger serrations on the pinnae margins, larger pinnae, fewer pinnae per frond, diagonally disposed pinnae, and fewer fronds per plant.

3 Drawing Figures

SUMMARY OF THE INVENTION

The new variety was discovered by me during the summer of 1980 while growing in a greenhouse of Jordan Station Wholesale Florist Ltd. at Jordan Station, Ontario, Canada, as a single plant among thousands of plants of *Nephrolepis exaltata* — Curly Boston variety. The plants from which the new variety was selected had been asexually reproduced at my request by tissue culture using runner tips supplied by me which were obtained from the Curly Boston variety. Accordingly, the new variety is believed to be a novel whole plant mutation of unknown causation which was derived from such Curly Boston variety. I was attracted to the new variety because of its highly attractive appearance and the distinctive combination of characteristics discussed hereafter.

I separated the distinctive plant of the present invention, placed it in a stock bench and multiplied it by separating plantlets from the stems. The new variety also has been asexually reproduced extensively by tissue culture. Observation of approximately five thousand plants of the new variety in various stages of growth has demonstrated that its distinctive characteristics are stable and are transmitted without change through succeeding propagations. No tendency has been observed for the characteristics of the new variety to revert to those of its parent.

The new and distinct variety of *Nephrolepis exaltata* of the present invention has been found to commonly exhibit the following combination of characteristics:

(a) a faster growth habit than the Curly Boston variety, (b) a mature 1-pinnate frond configuration which tends to be more oblong than that of the Curly Boston variety wherein the frond configuration is more tapered, (c) considerably more pronounced serrations on the pinnae margins than the Curly Boston variety, (d) larger pinnae than the Curly Boston variety, (e) when fully developed fewer pinnae per frond than the Curly Boston variety, (f) pinnae which tend to be slightly diagonally disposed along the midrib of the frond while the pinnae of the Curly Boston variety tend to be disposed at substantially right angles to the midrib of the frond, and (g) when fully developed bears fewer fronds per plant than the Curly Boston variety.

The new variety is particularly suited for growing as an attractive houseplant or for growing in a hanging basket.

The new variety has been designated the Eleanor cultivar. This name additionally has been registered with the Canadian Ornamental Plant Foundation.

BRIEF DESCRIPTION OF PHOTOGRAPHS

The accompanying photographs show for comparative purposes typical specimens of the new fern of the present invention. The plants illustrated were photographed during March, 1982 and were approximately six months of age. Such plants had been propagated by tissue culture and had been twice transplanted.

DETAILED DESCRIPTION

Figure 1:
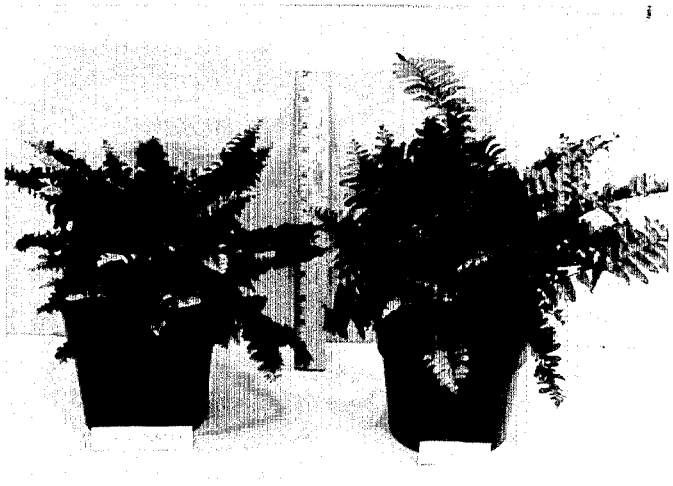
FIG. 1 illustrates on the right a plant of the Eleanor cultivar of the present invention and on the left for comparative purposes a Curly Boston plant. Each plant is growing in a six inch pot.
Figure 2:
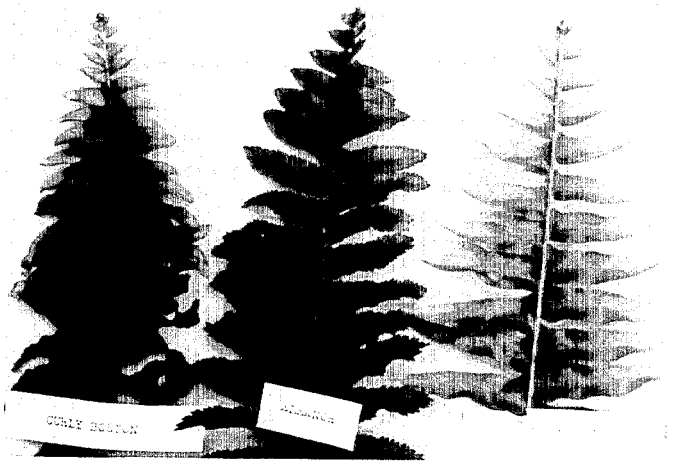
FIG. 2 illustrates in the center the distal end of a frond of the Eleanor cultivar of the present invention. On the left for comparative purposes is a distal end of a Curly Boston frond, and on the right for comparative purposes is the distal end of a Compacta frond.
Figure 3:
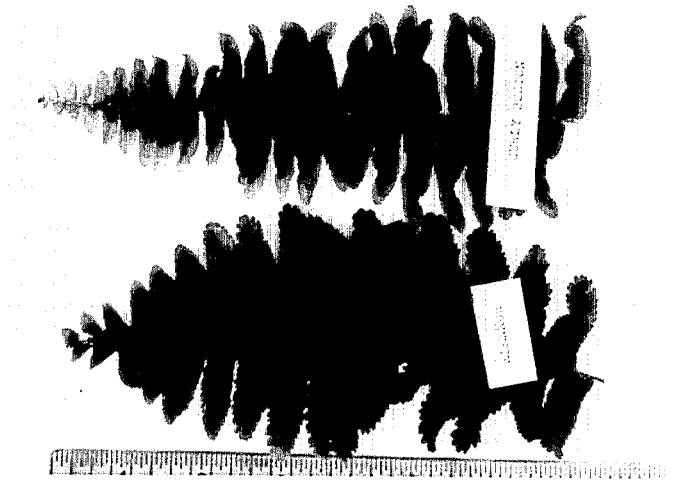
FIG. 3 illustrates in the lower portion of the photograph the distal approximately two-thirds of a frond of the Eleanor cultivar of the present invention, and in the upper portion of the photograph the distal approximately two-thirds of a Curly Boston frond.

The plants described were grown in greenhouses at Jordan Station, Ontario, Canada. Unless otherwise indicated the characteristics of the new variety substantially correspond to those of the Curly Boston variety. The color terms used herein are in accordance with their ordinary dictionary significance.

The new variety exhibits substantially faster growth than the Curly Boston variety. For instance, immediately following propagation such growth is estimated to be approximately thirty percent faster than that of the Curly Boston variety.

The fronds of the new variety are 1-pinnate as are those of Curly Boston. However, as illustrated in the photographs there are several significant differences between the fronds of the new variety and those of Curly Boston. For instance, the fronds of the new variety tend to be more oblong in configuration than those of the Curly Boston variety which bears fronds which tend to be more tapered.

The mature fronds of the new variety commonly are approximately 12 inches in length and approximately 2½ to 3½ inches in width, while those of Curly Boston commonly are approximately 10 inches in length and approximately 1¾ to 2¼ inches in width.

When fully developed the plants of the new variety commonly bear a lesser number of fronds per plant than Curly Boston. For instance, when observing fully developed plants of approximately the same age Curly Boston has been observed to form approximately 60 to 70 percent more fronds than the variety of the present invention. For example, during one comparison of approximately nine month old plants starting from tissue culture the Curly Boston possessed approximately 150 fronds per plant and the present variety possessed approximately 90 fronds per plant. During such count any frond less than one inch in length was disregarded and not included in the count.

Fully mature plants of the new variety when grown in pots commonly measure approximately 8 inches in height above the soil level and have a breadth of approximately 13 inches. On the contrary, fully mature Curly Boston plants when grown in pots tend to be slightly smaller and measure approximately 7 inches in height above the soil level and have a breadth of approximately 12 inches.

The pinnae (sometimes called leaflets or blades) on mature plants of the new variety as illustrated in the photographs have more pronounced serrations along their margins than those of Curly Boston. Such serrations of the new variety are two times or more as deep as those of the Curly Boston variety. Additionally, the overall size of the pinnae of the new variety tends to be larger than those of Curly Boston. The central pinnae along the midrib of the frond on mature plants of the new variety commonly are approximately 1½ to 1¾ inches in length and ½ inch width, while those of Curly Boston commonly are approximately 1 to 1½ inches in length and ⅜ inch in width.

The fronds of the new variety commonly bear fewer pinnae than Curly Boston. For instance, during one comparison of fully developed fronds the new variety averaged approximately 63 pinnae per frond while Curly Boston averaged approximately 77 pinnae per frond.

As illustrated in the photographs, the pinnae of the present invention tend to be slightly diagonally disposed along the midrib of the frond at an angle extending toward the distal end of the frond, while the pinnae of Curly Boston tend to be disposed at substantially right angles of the midrib of the frond. This could be characterized as being a slightly "herringbone" disposition.

The green coloration of the Curly Boston plant tends to appear slightly lighter and paler than that of the new variety particularly during the young growing stage when the tips are unfolding. Both plants have a glossy appearance which is distinctly different than that of *Nephrolepis exaltata* "Bostoniensis" or the common Boston fern.

Plants of the new variety appear to be more readily form rhizomes than Curly Boston.

The new variety has additionally been found to well adapt to changes in temperature. For instance, when grown in greenhouses at Jordan Station, Ontario, Canada, the ambient temperature has dropped to 45° F. at night and has risen to 85° F. in the daytime without deleterious results.

I claim:

1. A new and distinct variety of *Nephrolepis exaltata* which is believed to be a whole plant mutation of the Curly Boston variety, substantially as herein illustrated and described, characterized by (a) a faster growth habit than the Curly Boston variety, (b) a mature 1-pinnate frond configuration which tends to be more oblong than that of the Curly Boston variety wherein the frond configuration is more tapered, (c) considerably more pronounced serrations on the pinnae margins than the Curly Boston variety, (d) larger pinnae than the Curly Boston variety, (e) when fully developed fewer pinnae per frond than the Curly Boston variety, (f) pinnae which tend to be slightly diagonally disposed along the midrib of the frond while the pinnae of the Curly Boston variety tend to be disposed at substantially right angles to the midrib of the frond, and (g) when fully developed bears fewer fronds per plant than the Curly Boston variety.

* * * * *